(12) United States Patent
Brush et al.

(10) Patent No.: US 11,583,433 B2
(45) Date of Patent: Feb. 21, 2023

(54) MENSTRUAL DISC AND METHODS OF USE

(71) Applicant: Lyv Life Inc., San Francisco, CA (US)

(72) Inventors: Jennifer Brush, Walnut Creek, CA (US); Emma Sandrolini, Cupertino, CA (US); Marla Metz, San Diego, CA (US)

(73) Assignee: Lyv Life Inc., San Francisco, CA (US)

( * ) Notice: Subject to any disclaimer, the term of this patent is extended or adjusted under 35 U.S.C. 154(b) by 0 days.

(21) Appl. No.: 17/681,403

(22) Filed: Feb. 25, 2022

(65) Prior Publication Data
US 2022/0331147 A1   Oct. 20, 2022

Related U.S. Application Data

(63) Continuation of application No. 17/320,667, filed on May 14, 2021.

(60) Provisional application No. 63/176,685, filed on Apr. 19, 2021.

(51) Int. Cl.
*A61F 5/455* (2006.01)
*A61F 5/44* (2006.01)

(52) U.S. Cl.
CPC .......... *A61F 5/4553* (2013.01); *A61F 5/4404* (2013.01)

(58) Field of Classification Search
CPC ....... A61F 5/455; A61F 5/4553; A61F 5/4404
See application file for complete search history.

(56) References Cited

U.S. PATENT DOCUMENTS

| | | | | |
|---|---|---|---|---|
| 1,891,761 A * | 12/1932 | Goodard | ............... | A61F 5/4553 604/330 |
| 1,996,242 A * | 4/1935 | Hagedorn | ............. | A61F 5/4553 604/330 |
| 2,089,113 A * | 8/1937 | Chalmers | ............... | A61F 5/4553 D24/141 |
| 2,321,340 A * | 6/1943 | Waterbury | ............. | B29C 70/70 264/294 |
| 2,534,900 A * | 12/1950 | Chalmers | ............... | A61F 5/4553 604/330 |
| 2,616,426 A * | 11/1952 | Gordon | ................. | A61F 5/4553 604/330 |
| 2,836,177 A * | 5/1958 | Sells | ......................... | A61F 6/08 128/837 |
| 2,968,046 A * | 1/1961 | Duke | ..................... | A61G 9/006 604/149 |
| 3,128,767 A * | 4/1964 | Nolan | ....................... | A61F 6/08 604/330 |
| 3,371,664 A * | 3/1968 | Pleshette | ................... | A61F 6/08 128/837 |
| 3,404,682 A * | 10/1968 | Waldron | ................. | A61F 13/26 128/838 |
| 3,626,942 A * | 12/1971 | Waldron | ................... | A61F 6/08 604/330 |
| 3,841,333 A * | 10/1974 | Zalucki | ................. | A61F 5/4553 604/330 |

(Continued)

OTHER PUBLICATIONS

Flex, https://flexfits.com/ accessed on Oct. 26, 2021, The Flex Company, 6 pages.

(Continued)

*Primary Examiner* — Guy K Townsend
(74) *Attorney, Agent, or Firm* — J. Peter Paredes; Amin Talati Wasserman LLP

(57) ABSTRACT

Provided herein are systems, methods and apparatuses for a Menstrual disc.

16 Claims, 6 Drawing Sheets

(56) References Cited

U.S. PATENT DOCUMENTS

| | | | | |
|---|---|---|---|---|
| 3,845,766 A * | 11/1974 | Zoller | A61F 5/4553 | D24/141 |
| 4,031,886 A * | 6/1977 | Morhenn | A61F 2/005 | 128/837 |
| 4,200,102 A * | 4/1980 | Duhamel | A61F 5/451 | 604/353 |
| 4,270,539 A * | 6/1981 | Frosch | A61F 5/455 | 604/347 |
| 4,381,771 A * | 5/1983 | Gabbay | A61F 6/08 | 128/836 |
| 4,631,061 A * | 12/1986 | Martin | A61F 5/451 | 604/323 |
| 4,703,752 A * | 11/1987 | Gabbay | A61F 6/08 | 128/841 |
| 4,747,166 A * | 5/1988 | Kuntz | A61F 5/455 | 4/144.1 |
| 4,799,929 A * | 1/1989 | Knowles | A61F 5/4553 | 604/331 |
| 4,848,363 A * | 7/1989 | Cattanach | A61F 5/4553 | 128/834 |
| 4,886,508 A * | 12/1989 | Washington | A61F 5/455 | 604/347 |
| 4,895,170 A * | 1/1990 | Tlapek | A61F 6/08 | 128/832 |
| 4,961,436 A * | 10/1990 | Koch | A61F 6/08 | 128/834 |
| 5,049,144 A * | 9/1991 | Payton | A61F 5/455 | 600/574 |
| D323,212 S * | 1/1992 | Crawford | D24/141 | |
| 5,207,232 A * | 5/1993 | Shihata | A61F 6/08 | 128/838 |
| 5,295,984 A * | 3/1994 | Contente | A61F 5/4553 | 604/327 |
| 5,466,229 A * | 11/1995 | Elson | A61M 1/0023 | 604/323 |
| 5,674,212 A * | 10/1997 | Osborn, III | A61F 13/15 | 604/385.16 |
| 5,678,564 A * | 10/1997 | Lawrence | A61F 5/455 | 600/573 |
| 5,771,900 A * | 6/1998 | Austin | A61F 6/08 | 128/830 |
| 5,827,248 A * | 10/1998 | Crawford | A61F 5/4553 | 604/328 |
| 5,911,222 A * | 6/1999 | Lawrence | A61F 5/455 | 600/573 |
| 5,928,249 A * | 7/1999 | Saadat | A61B 17/42 | 606/119 |
| 5,947,992 A * | 9/1999 | Zadini | A61F 5/4553 | 606/191 |
| 6,117,163 A * | 9/2000 | Bierman | A61M 25/02 | 606/232 |
| 6,123,398 A * | 9/2000 | Arai | B60T 8/17552 | 303/151 |
| 6,126,616 A * | 10/2000 | Sanyal | A61B 10/0291 | 128/834 |
| 6,168,609 B1 * | 1/2001 | Kamen | A61F 5/4553 | 600/573 |
| 6,241,846 B1 * | 6/2001 | Contente | B29C 65/02 | 156/379 |
| 6,264,638 B1 * | 7/2001 | Contente | A61M 31/002 | 604/285 |
| 6,332,878 B1 * | 12/2001 | Wray | A61F 6/08 | 128/830 |
| 6,706,027 B2 * | 3/2004 | Harvie | A61F 5/453 | 604/326 |
| 6,732,384 B2 * | 5/2004 | Scott | A47K 11/12 | 4/144.1 |
| 6,740,066 B2 * | 5/2004 | Wolff | A61F 5/451 | 604/323 |
| 6,796,973 B1 * | 9/2004 | Contente | A61F 5/4553 | 128/832 |
| 6,918,899 B2 * | 7/2005 | Harvie | A61F 5/451 | 604/326 |
| 7,018,366 B2 * | 3/2006 | Easter | A61F 5/451 | 604/327 |
| 7,131,964 B2 * | 11/2006 | Harvie | A61F 5/455 | 604/326 |
| 7,135,012 B2 * | 11/2006 | Harvie | A61F 5/453 | 604/326 |
| 7,141,043 B2 * | 11/2006 | Harvie | A61F 5/451 | 604/326 |
| 7,220,250 B2 * | 5/2007 | Suzuki | A61F 5/451 | 604/328 |
| 7,335,189 B2 * | 2/2008 | Harvie | A61F 5/451 | 604/326 |
| 7,390,320 B2 * | 6/2008 | Machida | A61F 5/455 | 4/144.1 |
| 7,699,831 B2 * | 4/2010 | Bengtson | A61M 1/90 | 604/313 |
| 7,749,205 B2 * | 7/2010 | Tazoe | A61F 5/451 | 604/320 |
| 7,755,497 B2 * | 7/2010 | Wada | A61F 5/451 | 340/604 |
| 7,845,355 B2 * | 12/2010 | Moench | A61F 6/08 | 128/833 |
| 7,939,706 B2 * | 5/2011 | Okabe | A61F 5/4404 | 604/361 |
| 8,128,608 B2 * | 3/2012 | Thevenin | A61F 13/84 | 604/347 |
| 8,211,063 B2 * | 7/2012 | Bierman | A61M 25/02 | 604/179 |
| 8,287,508 B1 * | 10/2012 | Sanchez | A61F 5/4404 | 604/326 |
| 8,454,493 B2 * | 6/2013 | La Vean | A61F 6/08 | 600/33 |
| 8,546,639 B2 * | 10/2013 | Wada | A61F 5/4401 | 604/361 |
| 8,551,075 B2 * | 10/2013 | Bengtson | A61M 1/84 | 604/543 |
| 8,585,683 B2 * | 11/2013 | Bengtson | A61M 27/00 | 604/543 |
| 8,690,847 B2 * | 4/2014 | Norman | A61F 5/4553 | 604/327 |
| 8,795,248 B2 * | 8/2014 | Shihata | A61F 5/4553 | 604/385.18 |
| 9,028,460 B2 * | 5/2015 | Medeiros | A61F 5/451 | 604/347 |
| 9,173,799 B2 * | 11/2015 | Tanimoto | A61F 5/453 | |
| 9,357,982 B2 * | 6/2016 | Edmunds | A61F 13/2045 | |
| 10,016,308 B2 * | 7/2018 | Knox | A61F 13/00085 | |
| 10,226,376 B2 * | 3/2019 | Sanchez | A61F 5/455 | |
| D852,361 S * | 6/2019 | Sedic | D24/141 | |
| D852,362 S * | 6/2019 | Sedic | D24/141 | |
| 10,357,395 B2 * | 7/2019 | Miller | A61F 5/4404 | |
| 10,390,989 B2 * | 8/2019 | Sanchez | A61F 5/453 | |
| D864,390 S * | 10/2019 | Sedic | D24/141 | |
| D892,324 S * | 8/2020 | Yi | D24/141 | |
| D894,386 S * | 8/2020 | LeClerc | D24/141 | |
| D895,798 S * | 9/2020 | Newman | D24/141 | |
| D895,799 S * | 9/2020 | Newman | D24/141 | |
| D895,800 S * | 9/2020 | Knox | D24/141 | |
| 10,888,450 B2 * | 1/2021 | Sedic | A61F 5/4553 | |
| 10,893,975 B2 * | 1/2021 | Sedic | A61F 5/4553 | |
| 10,952,889 B2 * | 3/2021 | Newton | A61F 5/4404 | |
| 10,959,873 B2 * | 3/2021 | Wilson | A61F 5/4553 | |
| 10,973,496 B2 * | 4/2021 | Naseri | A61F 13/535 | |
| D923,785 S * | 6/2021 | Tsai | A61F 5/4553 | D24/141 |
| D928,946 S * | 8/2021 | Sanchez | D24/122 | |
| 2002/0019614 A1 * | 2/2002 | Woon | A61F 13/53747 | 604/378 |
| 2002/0087131 A1 * | 7/2002 | Wolff | A61B 5/20 | 604/327 |
| 2003/0195484 A1 * | 10/2003 | Harvie | A61F 5/455 | 604/355 |
| 2004/0127872 A1 * | 7/2004 | Petryk | A61F 13/49 | 604/382 |

(56) References Cited

U.S. PATENT DOCUMENTS

| | | | |
|---|---|---|---|
| 2004/0143229 A1* | 7/2004 | Easter | A61F 5/451 604/322 |
| 2004/0207530 A1* | 10/2004 | Nielsen | A61F 13/42 340/573.5 |
| 2004/0236292 A1* | 11/2004 | Tazoe | A61F 5/451 604/317 |
| 2004/0254547 A1* | 12/2004 | Okabe | A61F 5/455 604/317 |
| 2005/0033248 A1* | 2/2005 | Machida | A61F 5/455 604/327 |
| 2005/0070861 A1* | 3/2005 | Okabe | A61F 5/4404 604/327 |
| 2005/0070862 A1* | 3/2005 | Tazoe | A61F 5/441 604/327 |
| 2006/0015081 A1* | 1/2006 | Suzuki | A61F 5/451 604/329 |
| 2006/0155214 A1* | 7/2006 | Wightman | A61F 5/455 600/574 |
| 2007/0038194 A1* | 2/2007 | Wada | A61F 5/451 604/347 |
| 2007/0289598 A1* | 12/2007 | LaBarre | A61F 6/08 128/837 |
| 2008/0033386 A1* | 2/2008 | Okabe | A61F 5/4404 604/378 |
| 2008/0077097 A1* | 3/2008 | Chambers | A61F 5/4553 604/330 |
| 2008/0091153 A1* | 4/2008 | Harvie | A61F 5/451 604/318 |
| 2008/0200888 A1* | 8/2008 | Gooch | A61F 5/4553 604/330 |
| 2008/0287894 A1* | 11/2008 | Van Den Heuvel | A61F 5/455 604/327 |
| 2009/0192482 A1* | 7/2009 | Dodge, II | A61L 15/60 524/436 |
| 2009/0270822 A1* | 10/2009 | Medeiros | A61F 5/451 604/347 |
| 2010/0004612 A1* | 1/2010 | Thevenin | A61F 13/84 4/443 |
| 2010/0185168 A1* | 7/2010 | Graauw | A61F 5/4556 604/347 |
| 2010/0211032 A1* | 8/2010 | Tsai | A61F 5/453 604/319 |
| 2010/0242968 A1* | 9/2010 | Vean | A61F 6/08 128/830 |
| 2010/0312204 A1* | 12/2010 | Sheu | A61F 5/4408 604/330 |
| 2011/0040267 A1* | 2/2011 | Wada | A61F 5/4401 604/318 |
| 2011/0060300 A1* | 3/2011 | Weig | A61M 1/0003 604/319 |
| 2011/0172625 A1* | 7/2011 | Wada | A61F 13/42 604/385.01 |
| 2012/0103347 A1* | 5/2012 | Wheaton | A61F 5/453 128/885 |
| 2012/0245542 A1* | 9/2012 | Suzuki | A61F 13/84 374/45 |
| 2012/0253303 A1* | 10/2012 | Suzuki | A61F 13/42 374/45 |
| 2013/0006206 A1* | 1/2013 | Wada | A61F 13/535 604/385.01 |
| 2013/0110060 A1* | 5/2013 | Shihata | A61F 5/4553 604/330 |
| 2014/0012216 A1* | 1/2014 | Shaviv | A61F 5/4553 29/428 |
| 2014/0031774 A1* | 1/2014 | Bengtson | A61M 1/84 604/319 |
| 2014/0182051 A1* | 7/2014 | Tanimoto | A61G 9/006 4/144.3 |
| 2015/0164680 A1* | 6/2015 | Chen | A61F 13/8405 604/359 |
| 2015/0359660 A1* | 12/2015 | Harvie | A61F 5/441 604/351 |
| 2016/0106604 A1* | 4/2016 | Timm | A61F 13/84 604/385.01 |
| 2016/0278988 A1* | 9/2016 | Knox | A61F 15/005 |
| 2016/0367226 A1* | 12/2016 | Newton | A01K 23/005 |
| 2016/0374848 A1* | 12/2016 | Sanchez | A61F 5/453 604/319 |
| 2017/0007438 A1* | 1/2017 | Harvie | A61F 5/453 |
| 2017/0189222 A1* | 7/2017 | Lin | A61F 5/4553 |
| 2017/0266031 A1* | 9/2017 | Sanchez | A61F 5/4404 |
| 2017/0348139 A1* | 12/2017 | Newton | A61F 5/4404 |
| 2017/0360594 A1* | 12/2017 | Park | A61F 5/449 |
| 2018/0028349 A1* | 2/2018 | Newton | A61F 5/453 |
| 2018/0028350 A1* | 2/2018 | Wilson | A61F 5/4553 |
| 2018/0140458 A1* | 5/2018 | Brockway | A61F 5/4553 |
| 2018/0199874 A1* | 7/2018 | Hwang | A61B 10/0045 |
| 2018/0214298 A1* | 8/2018 | Medas | A61F 5/4553 |
| 2018/0228642 A1* | 8/2018 | Davis | A61F 5/4408 |
| 2019/0021898 A1* | 1/2019 | Ahn | A61F 5/4553 |
| 2019/0038451 A1* | 2/2019 | Harvie | A61F 5/441 |
| 2019/0083296 A1* | 3/2019 | Miller | A61F 5/4553 |
| 2019/0099166 A1* | 4/2019 | Naseri | A61F 13/15 |
| 2019/0125571 A1* | 5/2019 | Hu | A61F 5/4553 |
| 2019/0142624 A1* | 5/2019 | Sanchez | A61F 5/4404 604/319 |
| 2019/0192335 A1* | 6/2019 | Sedic | A61F 5/4553 |
| 2019/0201231 A1* | 7/2019 | Sedic | A61F 5/4553 |
| 2019/0224036 A1* | 7/2019 | Sanchez | A61F 5/443 |
| 2019/0282350 A1* | 9/2019 | Conti | A61B 10/0045 |
| 2019/0314191 A1* | 10/2019 | Bobarikin | A61F 5/4553 |
| 2019/0336318 A1* | 11/2019 | Kubo | A61F 5/455 |
| 2019/0358077 A1* | 11/2019 | Bauer | A61F 5/4553 |
| 2020/0022835 A1* | 1/2020 | Lloveras Maciá | A61F 5/4553 |
| 2020/0046544 A1* | 2/2020 | Godinez | A61F 5/451 |
| 2020/0046572 A1* | 2/2020 | Hwang | A61F 5/4404 |
| 2020/0078208 A1* | 3/2020 | Stoebe-Latham | A61F 5/4553 |
| 2020/0078209 A1* | 3/2020 | Stoebe-Latham | A61F 13/55105 |
| 2020/0179157 A1* | 6/2020 | Pitacco | A61F 5/44 |
| 2020/0214876 A1* | 7/2020 | Tsai | A61F 5/4553 |
| 2021/0069005 A1* | 3/2021 | Sanchez | A61F 5/443 |
| 2021/0113363 A1* | 4/2021 | Evans | A61F 5/4553 |
| 2021/0128342 A1* | 5/2021 | Miller | A61F 5/4553 |
| 2022/0331146 A1* | 10/2022 | Brush | A61F 5/4553 |

OTHER PUBLICATIONS

Intimina, https://www.intimina.com/ accessed on Oct. 26, 2021, LELOi AB, 27 pages.

Lumma, https://mylumma.com/ accessed on Oct. 26, 2021, Lummacups LLC, 9 pages.

Nixit, https://nixit.com/ accessed on Oct. 27, 2021, Nixit Limited, 7 pages.

Moonthlies, https://www.instagram.com/p/CLo9-fyLgKP/?hl=en [accessed on Jul. 18, 2022], 13 pages.

WIPO ISA/US, International Search Report and Written Opinion issued in corresponding application, PCT/US2022/025214, dated Jul. 14, 2022 (12 pages).

Cora Disc. Cora [online]. Date First Available Mar. 30, 2021 930.03.2021), Retrieved from the Internet: <https://www.amazon.com/Cora-Reuseable-Sustainable-Alternative-Eco-Friendly/dp/B091DDT562?ref_=ast_sto_dp&th=1> (13 pages) [accessed May 23, 2022].

* cited by examiner

MENSTRUAL DISC AND METHODS OF USE

CROSS REFERENCE TO RELATED APPLICATIONS

The present application is a continuation application and claims priority to U.S. nonprovisional application Ser. No. 17/320,667, filed May 14, 2021, which claims priority U.S. provisional application Ser. No. 63/176,685, filed Apr. 19, 2021, all herein incorporated by reference in their entireties.

BACKGROUND

The invention generally relates to reusable feminine hygiene products and their use in managing menstruation, and more specifically, to features that improve the insertion and removal process, overall comfort/fit, and capacity/wear time to improve the period experience and reduce environmental waste.

Menstrual Discs are an emerging category in reusable/sustainable period care and still somewhat undefined. The reusable period category includes menstrual cups, menstrual discs, reusable pads and period underwear. In addition, there are disposable menstrual discs that fulfill slightly different user needs. Since the category is nascent, there are only a few reusable menstrual discs in market currently and most brands are sold DTC and/or outside of the USA. There is not an established "state of the art" norm in discs. The disposable discs (produced by Flex/Softdisc) have the longest history in the category, but are not reusable, so do not resonate as strongly with consumers seeking more sustainable period care products Menstrual cups are more prevalent and there are many brands in-market. However, menstrual cups are also still emerging. That said, menstrual cups have gained traction in the past 4 years and are an entry point to the reusable products category. Sizing is one of the main pain points in menstrual cups. There are two main factors in selecting the right size cup: pelvic floor strength and cervix height. Most women are unaware of their own pelvic floor strength and cervix height. Thus, a universally sized disc would solve the sizing problem—and potentially increase the adoption of reusable products.

Lumma, Nixit, and Intimina all have reusable menstrual discs. Because the disc sits higher up in the vagina (in the vaginal fornix), many women have trouble removing the disc—citing examples of messy removal and/or not being able to get a firm grip on the edge of the disc. Only Lumma has attempted to innovate removal with the inclusion of a removal string. In our research, some women find the string too long/uncomfortable. One of the benefits of a menstrual disc is that it can remain in place and allow a woman to have sexual intercourse during her period. Lumma's removal string interfered with this benefit.

Both Nixit and Intimina's products are on the larger range of diameter and intimidating to some women (for insertion). Only Lumma has attempted small, medium and large sizing of the menstrual disc to address female anatomy. The diaphragm has a different purpose than the menstrual disc (preventing pregnancy versus collecting menses) but anatomically, sits in the same place in a woman's body, in the vaginal fornix.

In testing Nixit and Intimina, insertion was difficult. Intimina's soft rim made the disc flexible and easy to fold—but once inside the vagina, it was very difficult to open in the vaginal fornix and orient properly. Nixit's firm rim was easier to guide into place, but their thicker catch made the product uncomfortable once inserted.

The present invention attempts to solve these problems as well as others.

SUMMARY OF THE INVENTION

Provided herein are systems, methods and apparatuses for a Menstrual disc. In one embodiment, the Menstrual disc comprises an inner rim operably connected with a pull tab and a central catch portion, wherein the inner rim and the pull tab form a generally C-shape opening; the central catch portion operably connected with an outer rim including at least one grip portion and a curved top portion; wherein the outer rim is a semi-firm compliant rim that operates to fold inward towards an axis of the Menstrual disc to conform to a folded configuration from an open configuration; the axis runs from a front portion of the Menstrual disc to a back portion; the at least one grip portion is positioned perpendicular to the axis to permit folding of the Menstrual disc inwards towards the axis; and the central catch portion is operable to contain a menstrual fluid.

In one embodiment, a method of using a Menstrual disc comprises: folding the Menstrual disc to a folded configuration to a diameter D2 from a diameter D1 from an open configuration, wherein the diameter D2 of the folded configuration is between about 15 mm and about 35 mm; inserting the diameter D2 of the folded configuration through the vagina; tucking a front rim of the Menstrual disc up and behind the pubic bone to position the Menstrual disc; unfolding the Menstrual disc to the open configuration once the Menstrual disc is under the cervix; tucking a top rim portion of the Menstrual disc under the pubic bone such that the Menstrual Disc sits within the fornix without a seal; and collecting menstrual fluid with the Menstrual disc during a menstrual period.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

BRIEF DESCRIPTION OF THE DRAWINGS

In the accompanying figures, like elements are identified by like reference numerals among the several preferred embodiments of the present invention.

DETAILED DESCRIPTION OF THE INVENTION

Figure 1:
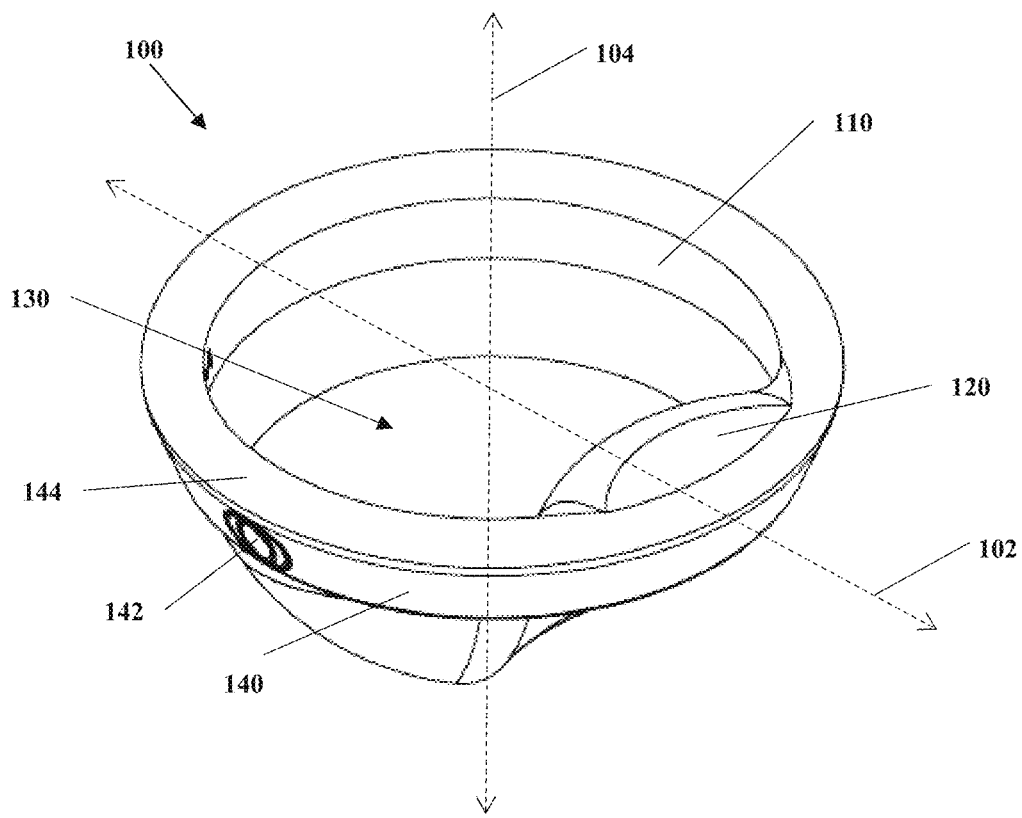
FIG. 1 is a perspective view of the Menstrual disc, according to one embodiment.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Generally speaking, the Menstrual disc is a reusable feminine hygiene product and the method of using the Menstrual disc is for managing menstruation, and more specifically, to features that improve the insertion and removal process, overall comfort/fit, and capacity/wear time to improve the period experience and reduce environmental waste.

The Menstrual disc is a simple, reusable alternative to pads and tampons designed to fit most women and stay in place comfortably. The Menstrual disc comprises a finger-width groove on the underside of the rim with a textured surface to improve grip, wherein the finger-width groove allows a user to easily hook their finger on the underside on the disc. This finger-width groove provides a method for emptying the Menstrual disc during wear without removal of the Menstrual disc from the vagina. Alternatively, the method provides for the emptying the Menstrual disc with removal of the Menstrual disc from the vagina, and reuse after cleaning and sanitizing.

The Menstrual disc comprises a diameter and a rim height specifically selected based on the anatomical features of the female body. Pelvic floor strength (influenced by age, childbirth, and weight, among other factors), cervix height (varies during the menstrual cycle) and fluid capacity are all size, property, and dimension considerations for the Menstrual disc. The diameter contribute to proper fit/comfort and universal sizing for most women, while the rim height and diameter are related to the capacity of the Menstrual disc. The diameter and rim height provide a fluid capacity to hold between about 30 ml to about 50 ml, alternatively about 47.5 mL of menstrual fluid for a comparatively long wear time up to about 12 hours. The Menstrual disc comprises the rim height with a thin catch, a side rim finger grip that provides the method of the folding and inserting the Menstrual disc through the vagina toward and contacting the cervix, and disposing the Menstrual disc within the fornix.

Figure 2:
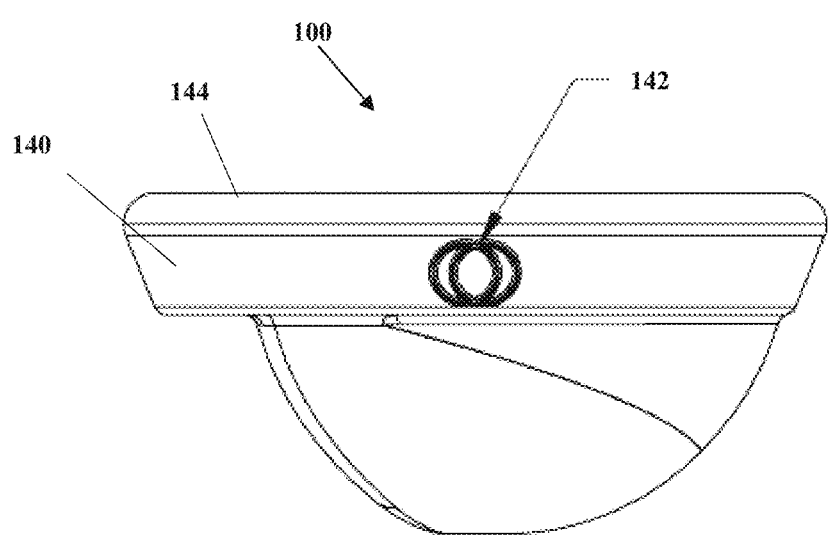
FIG. 2 is a side view of the Menstrual disc showing the grip portion, according to one embodiment.
Figure 12:
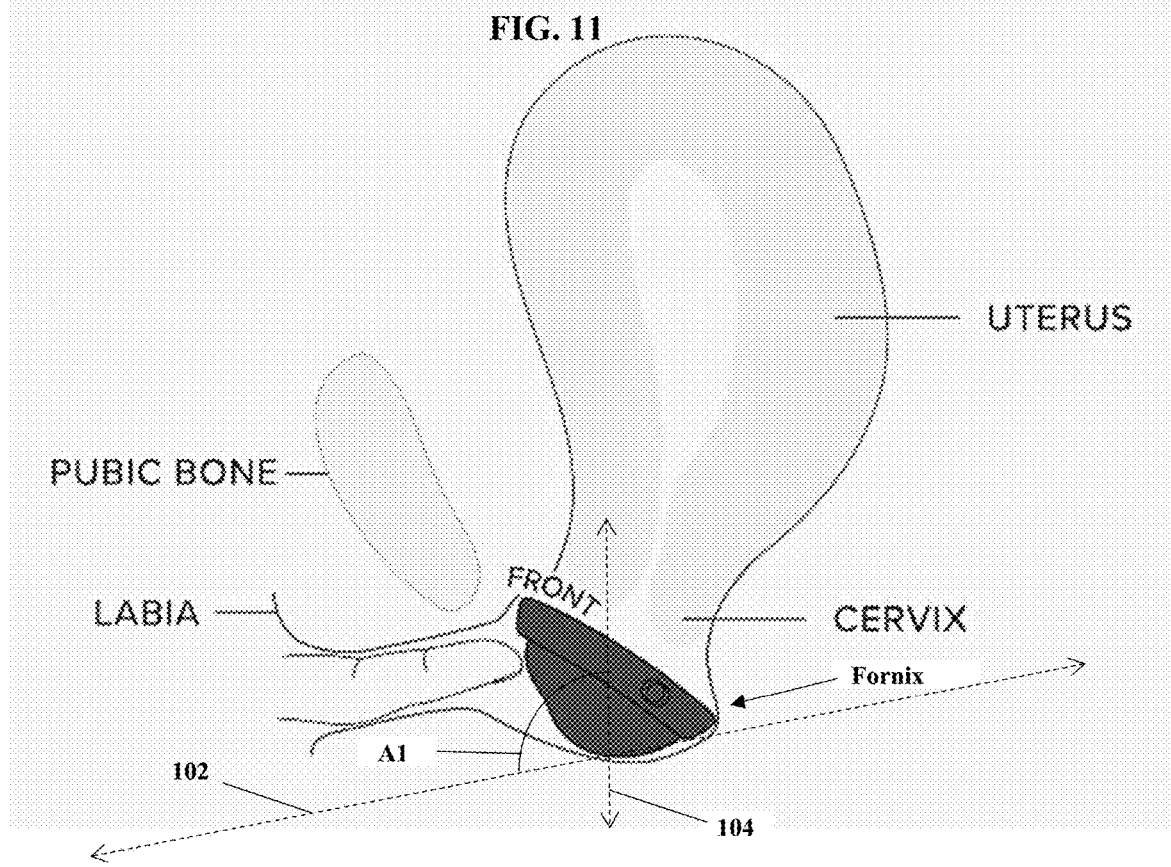
FIG. 12 is a schematic display of the cervix and fornix anatomy where the Menstrual disc is operably disposed.

As shown in FIG. 1, the Menstrual disc 100 is a generally circular configuration and comprises an inner rim 110 operably connected with a pull tab 120 and a central catch portion 130. The central catch portion 130 is operably connected with an outer rim 140 including at least one grip portion 142 and a curved top portion 144, as shown in FIG. 2. The outer rim 140 is a semi-firm compliant rim or semi-resilient or semi-elastic rim that operates to fold inward towards an axis 102 of the Menstrual disc to conform to a folded configuration from an open configuration, as shown in FIG. 1. The axis 102 runs from a front portion of the Menstrual disc 100 to a back portion and will substantially align with the sagittal plane of the human body when the Menstrual disc 100 is removably implanted or temporarily installed within vagina. The at least one grip portion 142 allows a user to fold the Menstrual disc along the axis 102 to the folded configuration and the grip portion 142 minimizes slippage during folding and insertion. The at least one grip portion 142 is positioned perpendicular to the axis 102 to permit folding of the Menstrual disc inwards towards axis 102. The at least one grip portion 142 includes a frictional component to allow a user to grip and fold the Menstrual disc into the folded configuration and insert the Menstrual disc without the user losing grip on the Menstrual disc. The folded configuration is operable for a user to insert the Menstrual disc and the open configuration is operable to cover the cervix within the fornix. The cervix projects into the vagina, and the circular trough formed at the upper end of the vagina around the cervix is the fornix. When removably implanted in the open configuration, the Menstrual disc 100 sits at an angle A1 off its longitudinal axis 104, as shown in FIG. 12. The central catch portion 130 is operable to contain, catch, or maintain menstrual fluid during a menstrual period and optimizes comfort for the user. The top portion of the pull tab 120 is operably connected to the top portion of the outer rim 140 to generate a non-annular opening or a generally C-shape opening of the Menstrual disc 100 in the open configuration.

Figure 3:
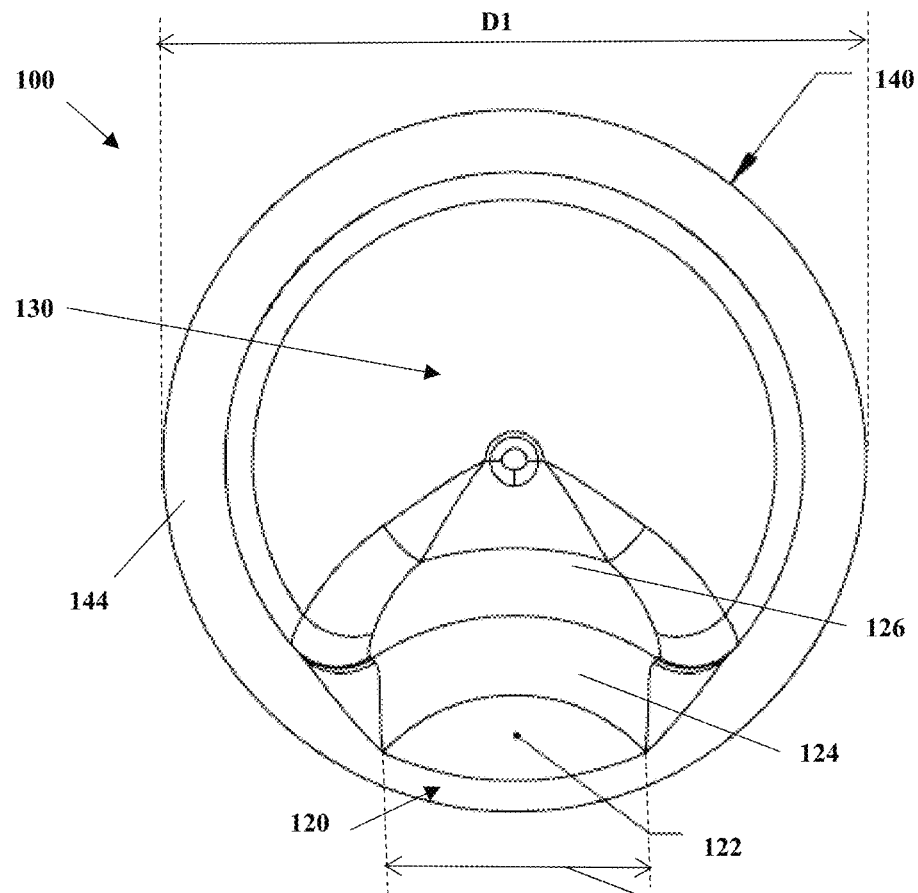
FIG. 3 is a top view of the Menstrual disc, according to one embodiment.
Figure 4:
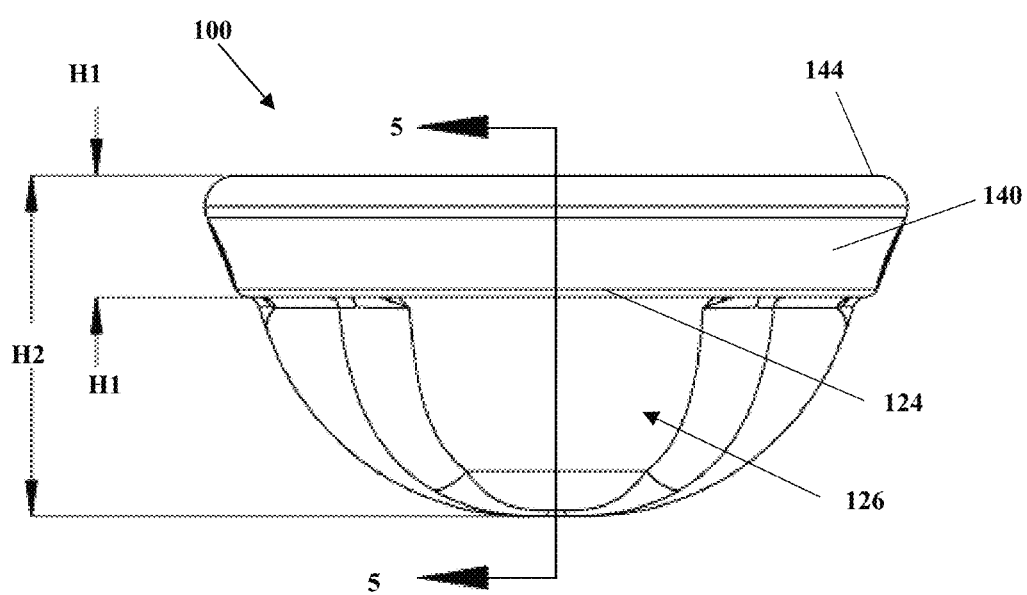
FIG. 4 is a front view of the Menstrual disc showing the pull tab, according to one embodiment.
Figure 5:
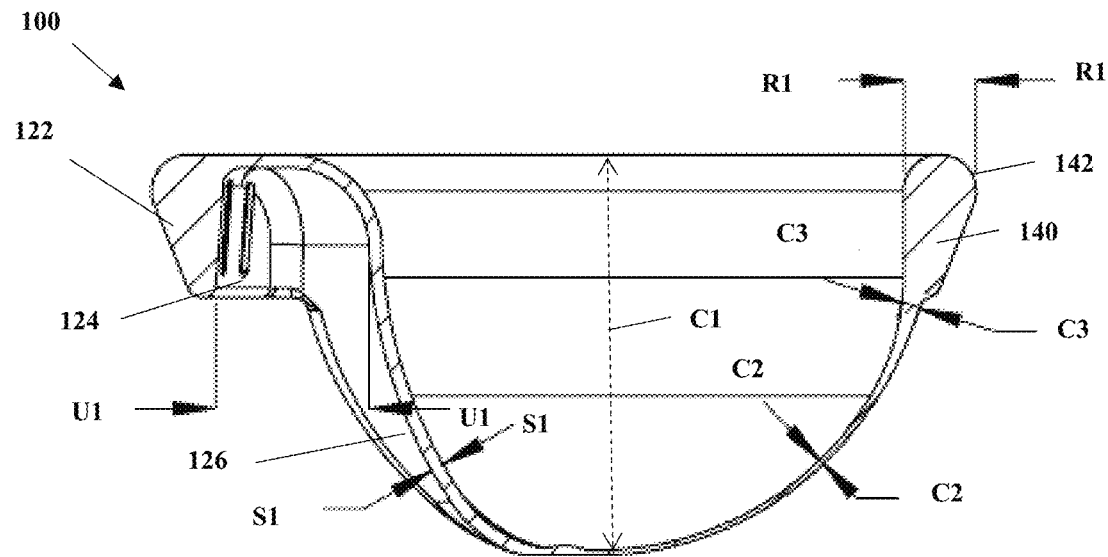
FIG. 5 is a cross-sectional view of the Menstrual disc taken along lines 5-5 from FIG. 4, according to one embodiment.

As shown in FIG. 3, the Menstrual disc 100 and the curved top portion 144 includes a diameter D1, the upper rim 110 includes a rim height H1, and the Menstrual disc 100 includes a disc height H2, as shown in FIG. 4. In one embodiment, the diameter D1 is between about 60 mm and 70 mm, alternatively, between about 62 mm and about 68 mm, alternatively between about 64 mm and about 66 mm, alternatively about 65 mm. In one embodiment, the rim height H1 is between about 9 mm and about 14 mm, alternatively, between about 10 mm and about 13 mm, alternatively, between about 11 mm and about 12 mm, alternatively about 11 mm. The disc height H2 is between about 28 mm and about 35 mm, alternatively, between about 29 mm and about 34 mm, alternatively, between about 30 mm and 33 mm, alternatively, about 31 mm. The curved top portion 144 includes a radius of curvature, as shown in FIG. 5. The radius of curvature between about 4 mm and about 8 mm, alternatively, between about 5 mm and about 7 mm, alternatively, about 6 mm. The radius of curvature is sized to permit smooth insertion of the Menstrual disc through the vagina opening and the cervix.

The upper rim 110 and the outer rim 140 include a rim thickness R1, as shown in FIG. 5. In one embodiment, R1 is between about 5.0 mm and about 6.0 mm, alternatively, between about 5.1 mm and about 5.9 mm, alternatively, between about 5.2 mm and about 5.8 mm, alternatively about 5.75 mm. In one embodiment, the ratio of the rim height H1 and rim thickness R1 is between about 0.9 and about 2.9, alternatively the ratio of H1:R1 is between about 1.2 and about 2.7, alternatively, between about 1.5 and about 2.5, alternatively, between about 1.7 and about 2.2, alternatively, about 1.83, alternatively, about 1.91. In one embodiment, the ratio of rim height H1 to rim thickness R1 is less than 2. The ratio of rim height H1 to rim thickness R1 is sized to provide optimal folding capability of the Cora Disc while permitting the rim to sit against the fornix during operation. The rim height H1 relates to the capacity of the disc; the rim thickness R1 relates to the firmness, which allows for an easier insertion experience and allows the user to get the disc in place more easily.

Figure 6:
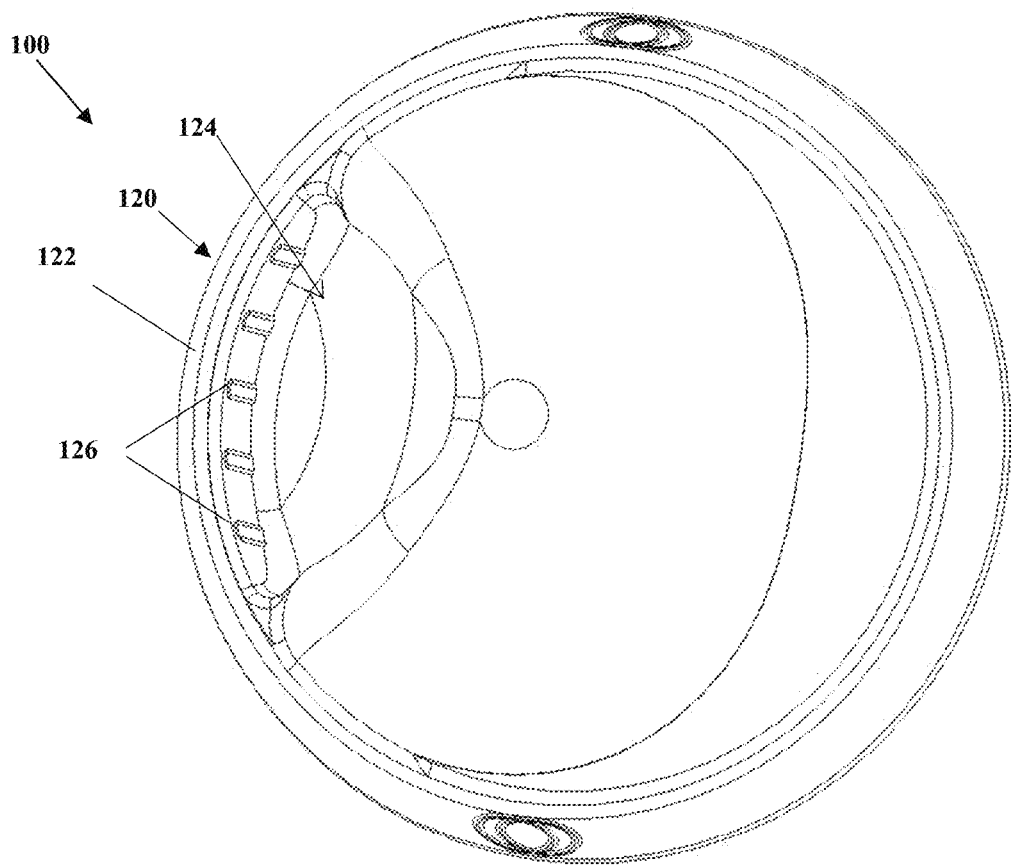
FIG. 6 is a bottom perspective view showing the Menstrual disc and the pull tab, according to one embodiment.
Figure 10:
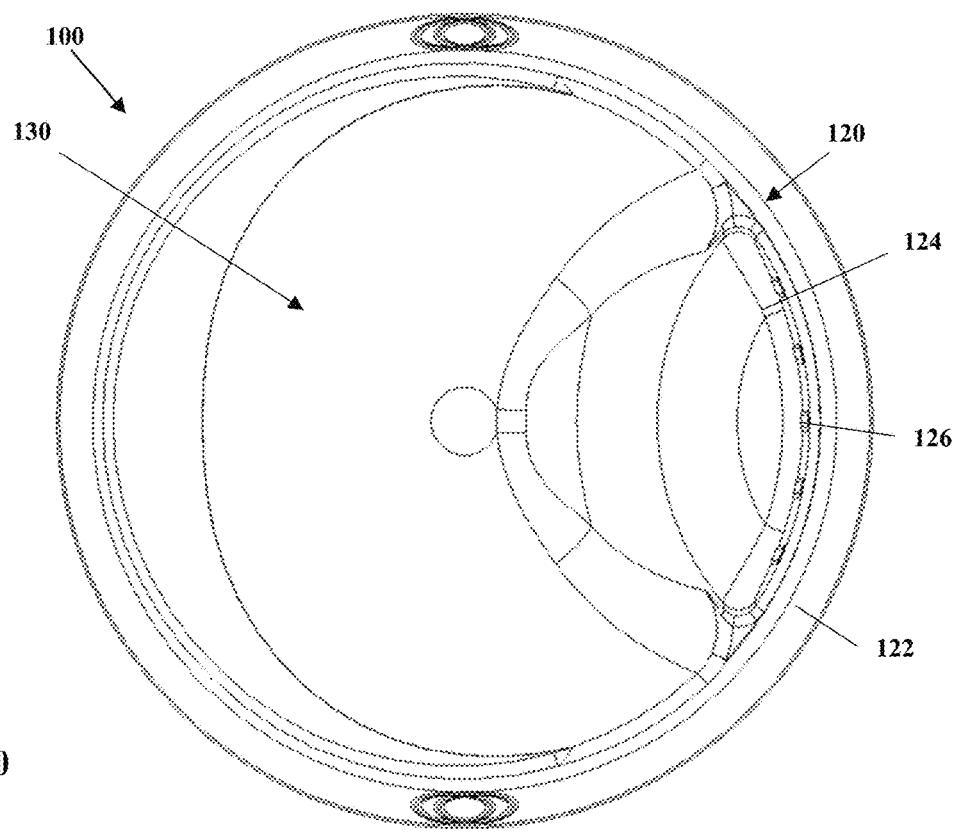
FIG. 10 is a bottom view of the Menstrual disc showing the pull tab, according to one embodiment.

The pull tab 120 includes a rim portion 122, an underside groove 124, and a sloped portion 126, as shown in FIG. 3. The rim portion 122 operably couples with the curved top portion 144 of the outer rim 140 to create the non-annular or generally C-shape opening of the Menstrual Disc 100. The rim portion 122 of the pull tab 120 provides additional structural support for the outer rim 140 when the Menstrual disc is in the open configuration and temporarily implanted. The underside groove 124 includes a width U1, as shown in FIG. 3, and a depth U2, as shown in FIG. 5. The width U1 and the depth U2 is a groove sized to permit a user to locate the Menstrual disc within the vagina and sized for the user's finger to grip the pull tab 120 and withdraw the Menstrual disc from the vagina. The width U1 and the depth U2 is also the approximate width and depth of the rim portion 122 of the pull tab 122. The width and depth of the rim portion 122 contributes to the structural support of the Menstrual disc in the open configuration when temporarily implanted. In one embodiment, the underside groove 124 includes a textured surface 126, as shown in FIGS. 6 and 10, to permit a user's fingertip to grip the pull tab 120 sufficiently within the vagina. The textured surface 126 includes a plurality of tabs designed with a raised geometric component to permit a user to grip the underside groove 124 when wet or covered by a fluid or menstrual fluid. In one embodiment, the raised geometric component includes a polygonal or quadrilateral profile. The pull tab 120 is oriented closest to the vaginal opening and the rim portion 122 along with the underside groove 124 allows the user to tilt the Menstrual disc in an upright position to avoid spilling menstrual fluid during removal of the Menstrual disc from the vagina. In one embodiment, width U1 and depth U2 are between about 9 mm and about 15 mm, alternatively, between about 10 mm and about 14 mm, alternatively about 11 m. The sloped portion 126 includes a width S1 between about 0.5 mm and about 1.5 mm, alternatively, between about 0.7 mm and about 1.2 mm, alternatively between about 0.9 and 1.1 mm. The sloped portion 126 is sized to operably connect with the central catch portion 130. The width S1 is sized to be greater than the thickness of the central catch portion 130, to permit greater stiffness when the pull tab 120 is pulled away from an axis of the Menstrual disc and allow menstrual fluid disposed in the central catch portion 130 to be disposed from the Menstrual disc when the pull tab 120 is engaged by a user. The rim portion 122 includes a triangular thickness profile, as shown in FIG. 5. The triangular thickness profile allows for the semi-rim stiffness of the outer rim 140 on the top portion of the Menstrual disc, while allowing for a thinner thickness on the bottom portion of the rim portion 122 to permit a user to deflect or grab the rim portion 122 of the pull tab 120. Each of the pull tab 120, underside groove 124, or textured surface 126 may be independently modified, sited, or shaped differently to meet the needs of the user, menstrual fluid, or anatomy.

As shown in FIG. 5, the central catch portion 130 includes a catch height C1 and a catch capacity. In one embodiment, the catch capacity is between about 35 ml and about 50 ml, alternatively, between about 46 ml and 48 ml, alternatively, about 47.5 ml. The central catch portion 130 sits flat within the vaginal canal. And the catch capacity is the volume of a cylinder ($\Pi\ r^2 h$). The volume of a cylinder calculation is used for the catch capacity of the Menstrual disc when not fully open once inserted into the vagina. The central catch portion 130 includes a catch thickness C2, as shown in FIG. 5. The catch thickness C2 is sized to permit the central catch portion 130 to rest comfortably within the vagina, allow the Menstrual disc to fold to the folded configuration, and secure when menstrual fluid is disposed within the central catch portion 130. In one embodiment, the catch thickness C2 is between about 0.1 mm and about 0.7 mm, alternatively, between about 0.2 mm and about 0.6 mm, alternatively, between about 0.3 mm and about 0.5 mm, alternatively, about 0.4 mm. The catch thickness C2 expands to a rim thickness C3 when the central catch portion 130 connects with the outer rim 140. In one embodiment, C3 is between about 0.8 mm and about 1.2 mm, alternatively, between about 0.9 mm and 1.1 mm, alternatively about 1.0 mm.

Figure 8:
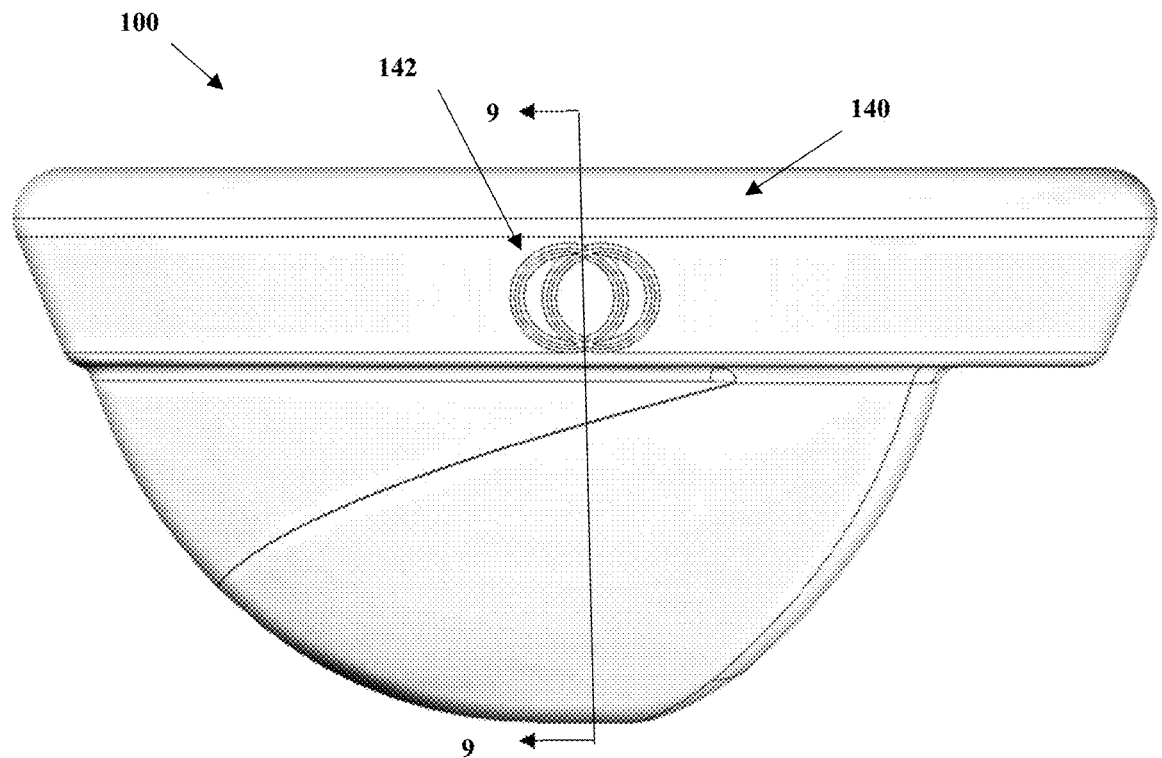
FIG. 8 is a side view of the Menstrual disc showing the grip portion, according to one embodiment.

FIG. 8 is a side view of the Menstrual disc 100 showing the grip portion 142, according to one embodiment. The grip portion 142 is comprised of at least two concentric circles that may be indentations on the outer rim 140 or raised portions on the outer rim 140 to provide the gripping action to flex the Menstrual disc to the folded configuration. The at least two concentric circles may be overlapping or may be separated by a distance. The at least two concentric circles may include smaller concentric circles within a larger concentric circle to provide additional gripping portions. The diameter of the concentric circles may include a diameter approximating the tip of finger. In one embodiment, the concentric circles include at least 2 smaller concentric circles confined with a larger concentric circle.

Figure 7:
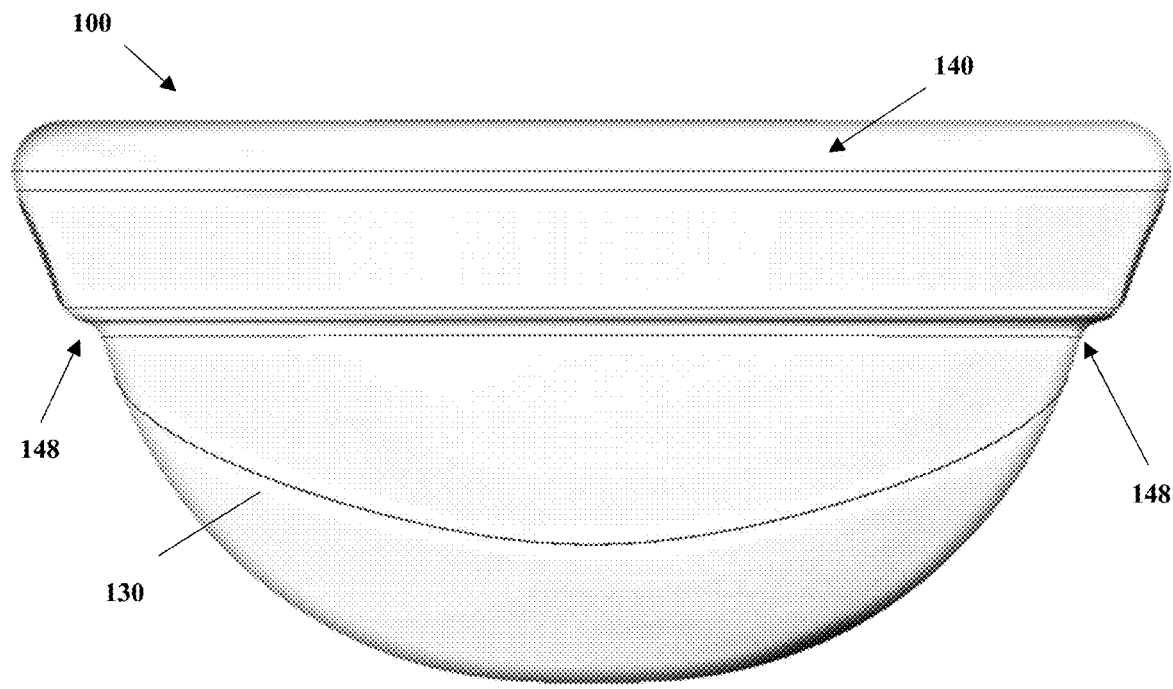
FIG. 7 is a back view of the Menstrual disc, according to one embodiment.
Figure 9:
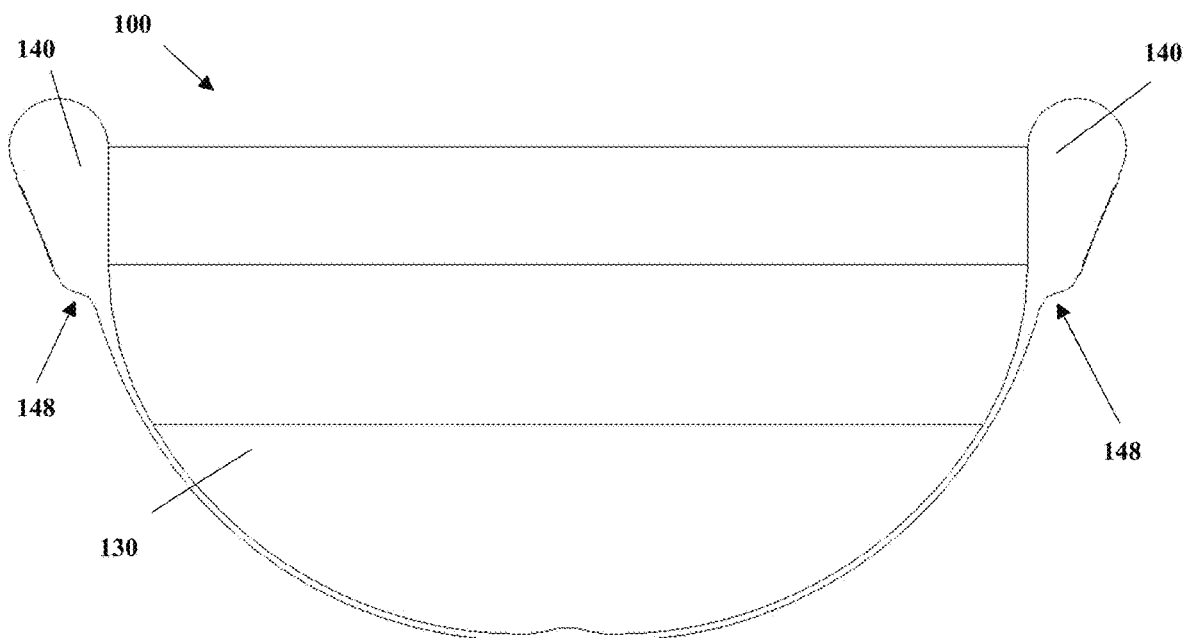
FIG. 9 is a cross-sectional view of the Menstrual disc taken along lines 9-9 from FIG. 8, according to one embodiment.

FIGS. 7 and 9 show that the outer rim 140 comprises an outer lip 148 disposed around the outer surface of the outer rim 140 and between the outer surface of the central catch 130. The outer lip 148 provides a seated surface in which to dispose the Menstrual disc on the fornix. The outer lip 148 may include a seated surface between about 0.1 mm and about 3.0 mm, alternatively between about 0.5 mm and 2.5 mm, alternatively, between about 0.9 mm and 2.0 mm. The semi-firm compliance of the outer rim 140 ensures the outer lip 148 and the seated surface maintain appropriate stiffness when the Menstrual disc is disposed on the fornix and when the central catch 130 includes menstrual fluid disposed therein.

Figure 11:
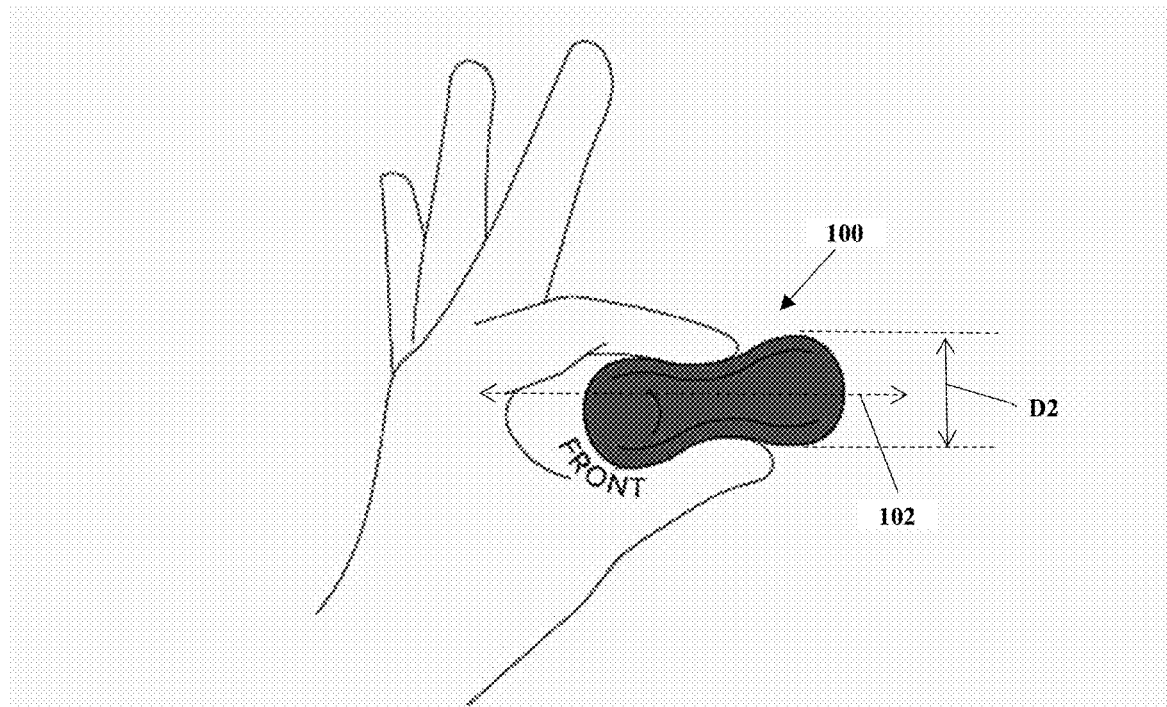
FIG. 11 is a depiction of the Menstrual disc disposed in the folded configuration, according to one embodiment.

In operation, the Menstrual disc is folded to the folded configuration and includes a diameter D2, as shown in FIG. 11. In one embodiment, the folded configuration is a generally FIG. 8 configuration. The diameter D2 of the folded configuration is between about 15 mm and about 35 mm, alternatively, between about 20 mm and about 30 mm. The diameter D2 of the folded configuration permits the Menstrual disc to be inserted through the vagina, as shown in FIG. 12. The user guides the back rim of the Menstrual disc into the vagina and tucks the front rim up and behind the pubic bone to position the Menstrual disc. Once the user is under the cervix, the Menstrual disc is unfolded to the open, semi-hemispheric configuration, where the top rim portion tucks under the pubic bone and sits in the fornix without requiring suction. Cervix height is the distance from the vaginal opening to the cervix and the cervix height is on average between about 3 and about 4 inches and varies to less than 3 and up to about 5 inches. In one embodiment, the Menstrual disc sits higher in the vaginal canal and rests within the fornix to receive or catch menstrual fluid during a menstrual period. When removably implanted or temporarily installed in the open configuration, the Menstrual disc 100 sits at an angle A1 off its longitudinal axis 104 and the axis 102 which sits on the sagittal plane at the base of posterior cervix, as shown in FIG. 12. In one embodiment, the open configuration of the Menstrual disc when removably implanted is a smaller open configuration due to the top rim portion being bent inward. The Menstrual disc may collect fluid for an extended period of time up to about 12 hours when disposed on the fornix. The Menstrual disc may empty a fluid while the Menstrual disc is disposed within the fornix by the user gripping the pull tab and tilting the pull tab downwards towards the vaginal opening to remove the fluid. The underside groove of the pull tab aids in the removal process by allowing a user to easily hook their finger on the underside on the Menstrual disc and the user gently slides the Menstrual disc out of the vagina.

In one embodiment, the Menstrual disc is made from medical grade silicone, polymer, rubber, or other elastomeric or biocompatible material. The menstrual disc is intended to be washable and reusable.

In an alternative embodiment, the Menstrual disc may be used for stress incontinence. The placement of the Menstrual disc inside the vagina puts gentle pressure on the bladder and could function similar to a pessary. A pessary is a prosthetic device that can be inserted into the vagina to support its internal structure. It's often used in the case of urinary incontinence and a vaginal or pelvic organ prolapse. The Menstrual disc could catch urine or other fluids. The Menstrual disc may also be used as a specimen collector to collect blood and/or vaginal, cervical and/or uterine discharge, including for diagnostic purposes.

The Menstrual disc is not limited to the preferred embodiments described herein. For example, the Menstrual disc is not restricted to human use. The Menstrual disc may be used to collect discharge from non-human primates and other animals, and/or for substance delivery for veterinary applications. For non-human primate and other veterinary uses, the dimensions of the devices would be sized or adapted to fit the dimensions of the vaginal canal of the animal concerned.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A menstrual disc, comprising:
an inner rim operably connected with a pull tab and a central catch portion, wherein the inner rim and the pull tab form a generally C-shape opening; the central catch portion operably connected with an outer rim including at least one grip portion and a curved top portion;
wherein the outer rim is a semi-firm and compliant rim that is configured to fold inward towards an axis of the menstrual disc to conform to a folded configuration from an open configuration, wherein the outer rim includes a rim thickness R1 and a rim height H1, and the ratio of the rim height H1 and rim thickness R1 is between about 0.9 and about 2.9;
wherein the axis runs from a front portion of the menstrual disc to a back portion; the at least one grip portion is positioned perpendicular to the axis to permit folding of the menstrual disc inwards towards the axis; and the central catch portion is configured to contain menstrual fluid in the open configuration and the folded configuration;
wherein the pull tab includes an underside groove and a sloped portion extending downward from the inner rim to the central catch position; the underside groove includes a width U1 and a depth U2, wherein the combination of the groove, the inner rim and a portion of the outer rim are sized to be configured to allow a user to grip two or more of the pull tab, the inner rim and the outer rim, to withdraw the menstrual disc from the vagina; the underside groove and the sloped portion configured to improve the grip of the user; and
wherein the top of the pull tab does not extend above the top of the outer rim and the inner rim.

2. The menstrual disc of claim 1, wherein the ratio of the rim height H1 and rim thickness R1 is about 1.83.

3. The menstrual disc of claim 1, wherein the thickness R1 is between about 5.0 mm and about 6.0 mm.

4. The menstrual disc of claim 2, wherein the menstrual disc includes a diameter D1, and the Menstrual disc includes a disc height H2, wherein the diameter D1 is between about 60 mm and 70 mm, the rim height H1 is between about 9 mm and about 14 mm, and the disc height H2 is between about 28 mm and about 35 mm.

5. The menstrual disc of claim 1, wherein the textured surface includes a plurality of tabs designed with a raised geometric component.

6. The menstrual disc of claim 1, wherein the width U1 and the depth U2 are between about 9 mm and about 15 mm; the sloped portion includes a width S1 between about 0.5 mm and about 1.5 mm, the width S1 is greater than a thickness of the central catch portion.

7. The menstrual disc of claim 6, wherein the rim portion includes a triangular thickness profile; the outer rim includes a semi-rim stiffness and a thinner thickness on a bottom portion of the rim portion.

8. The menstrual disc of claim 7, wherein the central catch portion includes a catch height C1 and a catch capacity; wherein the catch capacity is between about 35 ml and about 50 ml when the central catch portion sits within the vaginal canal; and the central catch portion includes a catch thickness C2 between about 0.1 mm and about 0.7 mm; the catch thickness C2 expands to a rim thickness C3 when the central catch portion connects with the outer rim; wherein the rim thickness C3 is between about 0.8 mm and about 1.2 mm.

9. The menstrual disc of claim 7, wherein the grip portion comprises at least two concentric circles.

10. The menstrual disc of claim 9, wherein the outer rim comprises an outer lip disposed around the outer surface of the outer rim and between the outer surface of the central catch.

11. Method of using a menstrual disc, comprising:
providing a menstrual disc according to claim 1;
folding the menstrual disc to the folded configuration to a diameter D2 from a diameter D1 from the open configuration, wherein the diameter D2 of the folded configuration is between about 15 mm and about 35 mm;
inserting the diameter D2 of the folded configuration into the vaginal canal;
tucking a front portion of the outer rim of the menstrual disc up and behind the pubic bone to position the menstrual disc within the vaginal canal under the cervix;
unfolding the menstrual disc to the open configuration once the menstrual disc is under the cervix;
resting a top rim portion of the menstrual disc within the fornix such that the menstrual disc sits within the fornix without a seal; and
containing menstrual fluid with the Menstrual disc in the open configuration and the folded configuration during a menstrual period.

12. The method of claim 11, collecting menstrual fluid for a time period up to about 12 hours.

13. The method of claim 11, further comprising emptying the menstrual fluid while the menstrual disc is disposed within the fornix by the user gripping a pull tab and tilting the pull tab downwards towards the vaginal opening to remove the menstrual fluid.

14. The method of claim 11, further comprising removing the menstrual disc from the vagina with an underside groove of the menstrual Disc by allowing a user to hook their finger on an underside on the menstrual disc and sliding the menstrual disc out of the vagina.

15. The method of claim 11, wherein the folded configuration is a generally figure 8 configuration.

16. The menstrual disc of claim 1, wherein the sloped portion includes a width S1 that is sized to be configured to have a greater width than the thickness of the central catch portion to permit greater stiffness that the thickness of the central catch portion.

\* \* \* \* \*